(12) United States Patent
Powell (10) Patent No.: US 6,606,519 B2
(45) Date of Patent: Aug. 12, 2003

(54) MICROCURRENT THERAPY DEVICE COMPONENTS STACK AND CONDUCTIVE PAD

(75) Inventor: Francis R. Powell, Cheshire, CT (US)

(73) Assignee: Newcare Products, LLC, Cheshire, CT (US)

(*) Notice: Subject to any disclaimer, the term of this patent is extended or adjusted under 35 U.S.C. 154(b) by 97 days.

(21) Appl. No.: 09/847,227

(22) Filed: May 2, 2001

(65) Prior Publication Data

US 2001/0056292 A1 Dec. 27, 2001

Related U.S. Application Data

(63) Continuation-in-part of application No. 09/595,146, filed on Jun. 16, 2000.
(60) Provisional application No. 60/231,018, filed on Sep. 8, 2000.

(51) Int. Cl.$^7$ ................................................. A61N 1/18
(52) U.S. Cl. ........................................................ 607/75
(58) Field of Search ............................. 607/2, 46, 48, 607/50, 63, 72, 74, 75, 115, 152

(56) References Cited

U.S. PATENT DOCUMENTS

| 4,121,594 | A |   | 10/1978 | Miller et al. |
|---|---|---|---|---|
| 4,474,570 | A |   | 10/1984 | Ariura et al. |
| 4,922,906 | A |   | 5/1990 | Takeuchi et al. |
| 4,982,742 | A | * | 1/1991 | Claude .................... 128/798 |
| 5,354,321 | A |   | 10/1994 | Berger |
| 5,423,874 | A |   | 6/1995 | D'Alerta |
| 5,578,065 | A | * | 11/1996 | Hattori et al. ................. 607/46 |
| 5,931,693 | A |   | 8/1999 | Yamazaki |
| 6,037,879 | A | * | 3/2000 | Tuttle .................... 340/825.54 |
| 6,218,044 | B1 | * | 4/2001 | Suzuka ........................ 429/175 |
| 6,263,226 | B1 | * | 7/2001 | Axelgaard et al. .......... 600/391 |
| 6,445,955 | B1 | * | 9/2002 | Michelson et al. ........... 607/46 |

OTHER PUBLICATIONS

Web Pages from Pain T.E.M.—The Analgesic for the New Millenium printed Nov. 7, 2000 and Nov. 14, 2000 as indicated.
1) www.backandbodycenter.com/products–PTEM..htm; Article from Special Issue of Bio/Tech News on Pain T.E.M. Copyright 1993 starts on this page and continues on pages listed below as 2)–6). For the convenience of the examiner a Word document downloaded in response to link on this page is provided in what is thought to be a more convenient format.
2) www.backandbodycenter.com/products–PTEM–BTNews–01.htm.
3) www.backandbodycenter.com/products–PTEM–BTNews–02.htm.
4) www.backandbodycenter.com/products–PTEM–BTNews–03.htm.
5) www.backandbodycenter.com/products–PTEM–BTNews–04.htm.
6) www.backandbodycenter.com/products–PTEM–BTNews–05.htm linked to Bio–Tech News, printed Nov. 8, 2000
7) Word download of Bio/Tech News.

(List continued on next page.)

Primary Examiner—Jeffrey R. Jastrzab
Assistant Examiner—Frances P. Oropeza
(74) Attorney, Agent, or Firm—Daniels Daniels & Verdonik, P.A.; Kevin E. Flynn (57) ABSTRACT

A microcurrent therapy device (MCTD) for use in applying a DC current of less than one milliampere between two conductive pads through the tissue of a therapy recipient has an electronic stack that can be placed in electrical connection with the user's skin and thus in electrical connection with the other skin contact plate, a profile minimizing system using an off the shelf "coin" battery within the electronic stack, and a battery clip used in conjunction with a coin battery and the circuit board of the MCTD.

9 Claims, 7 Drawing Sheets

OTHER PUBLICATIONS

AA) Photocopy of the faces of a box for IGIÁ® Electro–Fit Mini–Wireless Massage Device.
AB) Web page for IGIÁ® Electro–Fit Wireless, www.igia.com/cfm/prduct.cfm?ID=AT6703 printed Jan. 15, 2001.
AC) Web page for IGIÁ® Electro–Fit, www.igia.com/cfm/prduct.cfm?ID=AT6688 printed Jan. 15, 2001.
AD) Web page for IGIÁ® Electro–Accusage, www.igia.com/cfm/prduct.cfm?ID=AT6701 printed Jan. 15, 2001.
AE) Web page for IGIÁ® Electro–Sage 8, www.igia.com/cfm/prduct/cfm?ID=AT6717 printed Jan. 15, 2001.
AF) Web page for IGIÁ® Micro–sage 8, www.igia.com/cfm/prduct/cfm?ID=AT7182 printed Jan. 15, 2001.
Web page www.bmls.com/fmicroplus.html for Biomedical Life Systems, Inc., printed Jan. 15, 2001.
A series of pages from Electromedical Resources, Inc., www.elecmedres.com printed Jan. 15, 2001. Pages provided for a number of products distributed by this site include:
CA) Web page with Introduction & Mission Statement at ./intro.htm.
CB) Web page with a list of Products & Services at ./products.htm.
CC) Web pages of Muscle and/or Peripheral Nerve Stimulation devices; at . . . /mans.htm & mansbox.jpg.
CD) Web page with a device for Electronic Dental Anesthesia (EDA) at . . . /reftect.htm.
CE) Web page noting that the availability of Galvanic Stimulation devices at . . . /galvanic.htm.
CF) Web page noting the use of clinical EMG therapy for pain management and muscle rehabilitation at . . . /emg.htm.
CG) Web page showing devices used for muscle stimulation at . . . /muscle.htm.
CH) Web page showing a device for use as a Bone Growth Stimulator at . . . /bgs.htm.
CI) Web page showing Interferential Stimulation at . . . /interferential.htm.
CJ) Web page showing a device for using microamperage instead of millamperage to drive it's current into the effected area at . . . /microcurrent.htm.
CK) Web page showing various TENS devices (transcutaneous electrical nerve stimulators) at . . . /tens.htm.
Printout of various web pages from www.toneamatic.com, printed Jan. 15, 2001. These pages show a number of devices used to muscle stimulation.
DA) Web page of Tone–a–Matic® Body Building Fitness Machines (EMS), at www.toneamatic.com/front.htm.
DB) Web page explaining what Tone–a–Matic® is at www.toneamatic.com/What is EMS.htm.
U.S. Food and Drug Administration—Center for Devices and Radiological Health Database Printout dated May 7, 2001 for device name: Ultima XS Microcurrent Tens by American Imex, Irvine, California. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Ultima XS, Modifications by American Imex, Irvine, California. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Microcare™ by American Imex, Irvine, California. Page of material printed from World Wide Web concerning Microcare™ (1 page). http://www.accessdata.fda.gov/scripts/cdrh/cfdocs/cfPMN/pmn.cfm.

U.S. Food and Drug Aministration—Center for Devices and Radiological Health Database Printout dated May 7, 2001 for device name: Micro II Microcurrent Tens by Apex Medical Group, Taipei, Taiwan. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Multi–Stim Tens, AP–101081T by Apex Medical Group, Taipei, Taiwan. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Electro–Acuscope 85 by Biomedical Design Instruments, Los Angeles, California. Pages of material printed from World Wide Web concerning Electro–Acuscope 80 (3 pages); Applicant believes this product to be of the same product family. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Electro–Nerve Stimulator Tens Model Micro Plus–A by Biomedical Design Instruments, Los Angeles, California. Page of material printed from World Wide Web concerning Micro Plus™ (1 page). http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Dynatron 200 Microcurrent by Dynatronics Corp., Salt Lake, Utah. Pages of material printed from World Wide Web concerning Dynatronics rehabilitation products (4 pages); Applicant believes this product to be of the same product family http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Neuron II and Microtens by Datran Corp., New Haven Connecticut. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Alpha–Stim CS by Electomedical Products, Inc., Hawthorne, California. Pages of material printed from World Wide Web concerning Alpha Stim Technology (6 pages). http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Globalcare Micro 11 and Microcare (Tens) by Globalcare International, Inc., Holyoke, Massachusetts. http://www.accessdata.fda.gov/scripts/cdrh/cfdocs/cfPMN/pmn.cfm.
U.S. Food and Drug Administration—Center for Devices and Radiological Health Database Printout dated May 7, 2001 for device name: Globalcare Micro 11 by GlobalCare International, Inc., Holyoke, Massachusetts. http://www.accessdata.fda.gov/scripts/cdrh/cfdocs/cfPMN/pmn.cfm.
U.S. Food and Drug Administration—Center for Devices and Radiological Health Database Printout dated May 2, 2001 for device name: Team MC by Henley International, Sugar Land, Texas. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Team–MC II by Henley International, Sugar Land, Texas. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Home Microcurrent HMC by Medical Devices, Inc., St. Paul, Minnesota. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Medipoint by Medipoint Ltd., New York, New York. 501(K) summary for 501(K) application K9819761. (5 pages) http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Med–4000 by Micro Current Technology, Inc., Seattle, Washington. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Acutron Mentor Model 961 by Microcurrent Research, Inc., Phoenix, Arizona. 501(K) summary for 501(K) application K9819761 (6 pages) and Pages of material printed from World Wide Web concerning Acutron Mentor (2 pages) http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Microstim 100 Model 2C by Microstim, Inc., Penngrove, California. Pages of material printed from World Wide Web concerning Microstim 400–III (2 pages). http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Micro Mode–Trans Electrical Neural Stimulator by Mod Mode Medical, Ormond Beach, Florida. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: My–O–Matic 50001 by Monad Corp., Pomono, California. ). Applicant believes this product to be of the same product family. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MENS–O–MATIC 1 by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MENS–O–MATIC 2000 by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MiCRO DERM by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001, for device name: MENS–O–MATIC 3000 by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MENS–O–MATIC 1X and MENS–O–MATIC 2XS by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001, for device name: MENS FREEDOM MICRO by Monad Corp., Pomono, California. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MENS 2000D by Monad Corp., Pomono, California. Pages of material printed from World Wide Web concerning MENS–O–MATIC II and MENS–O–MATIC IV (2 pages). http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: VECTRA PRO MODELS 2 and 4 by Chattanooga Group, Inc., Hixson, Texas. Pages of material printed from World wide Web concerning VECTRA™ PRO Model 4 (3 pages); printed Jun. 5, 2001; http://www.chattanoogagroup.com/proddetails.asp?pn=8350 Pages of material printed from World wide Web concerning VECTRA™ PRO Model 2 (3 pages); printed Jun. 5, 2001; http://www.chattanoogagroup.com/proddetails.asp?pn=8351.

U.S. Food and Drug Administration—Center for Devices and Radiological Health Database Printout dated May 7, 2001 for device name: Intelect by Chattanooga Group, Inc., Hixson, Texas. Page of material printed from World Wide Web concerning Intelect 2 (1 page); printed Jun. 5, 2001; http://www.chattanoogagroup.com/proddetails.asp?pn=7550.

U.S. Food and Drug Administration—Center for Devices and Radiological Health Database Printout dated May 7, 2001 for device name: Vectra Stim Models 200 and 400 by Chattanooga Group, Inc., Hixson, Texas. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: Intelect 600MP by Chattanooga Group, Inc., Hixson, Texas. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MICRO–Q by Quantitative Medicine, Inc. http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: MICRO 100, 200, 300, & 400 Tens by Skylark Device Co., Ltd., Taipei, Taiwan. Applicant believes this product to be of the same product family http://www.accessdata.fda.gov/scripts/cdrh/cfdocs/cfPMN/pmn.cfm.

U.S. Food and Drug Administration—Center for Devices and Radiological Health Database Printout dated May 7, 2001 for device name: GB–1002 Tens with Massage by Skylark Device Co., Ltd., Taipei, Taiwan. Pages of material printed from World Wide Web concerning Skylark, Inc. diagnostic, Treatment, Personal Care, Functional Feed–body tone, and Accessory and Consuming Material systems (6 pages). http://www.accessdata.fda.gov/scripts/cdrh/cfdocs/cfPMN/pmn.cfm.

U.S. Food and Drug Administration—Center for Devices and Radiological Health Database Printout dated Jun. 5, 2001 for device name: TRIO 300 by Ito Co, Ltd., Rockville, Maryland. 501(K) summary for 501(k) application K990987. (6 pages) http://www.accessdata.fda.gov/scripts/cdrh/cfdocs/cfPMN/pmn.cfm.

* cited by examiner-

MICROCURRENT THERAPY DEVICE COMPONENTS STACK AND CONDUCTIVE PAD

PRIORITY

This application is a continuation-in-part application of co-pending U.S. patent application Ser. No. 09/595,146 filed Jun. 16, 2000. This application also claims priority from co-pending U.S. Provisional Application Ser. No. 60/231018 filed Sep. 8, 2000. Both applications are incorporated by reference.

BACKGROUND OF THE INVENTION

1. Introduction

This invention is in the field of devices used to apply microcurrent treatment such as used for application of microcurrent treatment to portions of the human body. Microcurrent therapy is distinct from other methods of applying electromagnetic fields to living tissue. The name microcurrent therapy stems from the use of microamperes as opposed to milliamperes used in TENS devices such as the D'Alerta device disclosed below.

This invention is directed to providing a device that is useful in microcurrent therapy. The device is then used then used in a biological application to provide relief or treatment to tissue and joints. In order to provide context to the use of the invention, the description will include references to the use of the device in connection with the extended application of a microcurrent running through the tissue of the user of the device. Analogous to the variations in the response of various individuals with various maladies to drug therapy, there are many variations in individual response to microcurrent therapy. Although the present invention provides a device that can provide a sustained current flow within a desired microcurrent range, this does not remove all of the other biological variations between users.

One of the requirements of the patent process is to provide the best mode of using the invention. The inventor of the present invention has not invented microcurrent therapy nor has the inventor personally directed controlled studies that determined optimal placement and current application regimes for microcurrent devices. Thus the best mode provided by the inventor for the present invention relates to the microcurrent therapy device and the method of indicating a current flow through the tissue. It is expected that as this field is further developed by those skilled in developing such microcurrent therapies, that one skilled in the art of making microcurrent therapy devices will be able to adapt the disclosed invention to provide the specific requested microcurrent therapy.

2. Description of the Prior Art

A device for use in the application of therapeutic microcurrent to tissue is disclosed in U.S. Pat. No. 5,354,321 to Mario Berger. The '321 patent discloses a Patch Arrangement for Galvanic Treatment. The Abstract of the Berger patent asserts that the '321 invention is based on the object to employ electrotherapy through stable galvanization without an external voltage source to provide an efficient and practical device. Rather than repeat all that is taught in the Berger patent, the U.S. Pat. No. 5,354,321 is hereby incorporated by reference.

The Berger patent builds on earlier inventions to apply metal plates to the surface of the skin on both sides of the effected area. By selecting a particular arrangement of dissimilar metals and insulators, one can produce a flow of current through skin and the tissue below the skin as this portion of the body provides an electric bridge between plates of dissimilar metals. The circuit path between the two dissimilar metal plates allows a small current on the order of microcurrents to flow through the tissue until this Galvanic current is no longer present. The Berger patent asserts that the use of a series of pairs of dissimilar metals can be used to improve the prior art devices by increasing the Galvanic current effect.

As noted in column three of the Berger '321 patent, there may be times where an electrically conductive material will be applied between the skin and the metal electrodes in order to reduce the electrical resistance between the metal electrodes and the skin. The material will need to be electrically conductive but can be any one of a number of materials that can be left in contact with the skin such as a material containing or soaked with an electrolyte. Perspiration carries various electrolytes. Thus a piece of fabric soaked in perspiration would serve as an electrically conductive material.

Unfortunately, skin, tissue, and perspiration are not manufactured items with constant electrical properties. These materials vary both between individuals and even at different times and places for the same individual. An individual that has dry skin in the winter is likely to have different electrical properties in the skin than the same person would have in the summer while playing tennis and perspiring heavily. The use of a conductive gel helps with dry skin but adds its own source of variability in its level to conductivity. Various gels are used for medical reasons to promote "good contact" between the skin and various monitoring devices. While it may not matter the specific electrical conductivity of a dab of gel for use in getting "good contact" for a monitoring device, the same is not true for a microampere current flow that is intended to be kept within a narrow range of current flow rates.

Since there are several factors which lead to variability in the electrical properties of skin, tissue, and the gels used to promote good contact, it then follows that the electrical properties of the skin and tissue vary from one person to another and even for one person from one week to another. The variation in electrical properties cause variations in the flow rate of current and the effective life of the current source for therapeutic device. The use of various types of conductive gels, the thickness and uniformity of application of the gel, the amount of perspiration on the skin—all add to the variability. Yet, another source of variability is the cleanliness of the surface of the metal pads in the Gerber device.

The net effect of all these variations causes considerable variation in current flow. In some cases the current flow from a Galvanic device can be below the level of current flow desired for therapeutic action. In other cases the same device can provide a current flow that not only exceeds the desired levels but actually causes a painful burning sensation.

U.S. Pat. No. 5,423,874 to D'Alerta discloses a Patch for Applying Pain Reducing Electrical Energy to the Body. The D'Alerta patent describes another type of device, a TENS device that is used to block the sensation of pain without any rejuvenative effect to the tissue. This D'Alerta '874 patent is incorporated by reference into this description but will be briefly described.

One of the many differences between the '874 device and the Berger Galvanic device in that the '874 includes "on-board circuitry" to provide additional control beyond the constant application of a decaying Galvanic voltage potential. The '874 patent includes an integrated circuit and other circuitry for creation of a series of 50 volt square waves. (In other words the voltage quickly rises to 50 volts DC, is maintained at that voltage for a fixed period of time, falls quickly to 0 volts and then stays at 0 volts for a fixed period of time before repeating the pattern.)

Although the D'Alerta device is for delivering current at milliampere rather than microampere levels (approximately 1000×the levels of current delivered in a microcurrent device), the D'Alerta device is included here to highlight a use of an LED indicator light. The D'Alerta device provides a 50 volt pulse to the skin and is easily perceived by the user. The LED light as placed in FIG. 7 as Element CR1 indicates whether the timing clock signal on pin 3 of IC1 and the battery V1 are operating. Thus, the indicator LED of the D'Alerta device is not in line with the current path through the user between the Anode Pad and the Cathode Pad and thus does not indicate the successful application of current through the user's skin.

3. Problems with Prior Art Solutions

The name microcurrent therapy stems from the use of microamperes as opposed to milliamperes used in TENS devices. One of the results of using such low current levels is that the user of a microcurrent therapy device ("MCTD") is often unable to tell when the device is applying a therapeutic dose of microcurrent or when the device is simply not working at all. While it is desirable that the operation of the MCTD does not cause discomfort to the person receiving therapy, there are two major problems with being imperceptible the user.

The first problem a false positive conclusion that a MCTD unit that has been damaged, improperly used, or used beyond its useful life will be used for an extended period of time without any application of microcurrent to the target site. False positive conclusions are harmful in that they interfere with effective treatment and lead users to believe that microcurrent therapy will not be useful to the user.

The second problem is a false negative conclusion that some users will mistakenly believe that a functioning MCTD is not operating and will then remove and discard functional MCTD units. If a new user receives a device that does not give any readily perceptible indication that the device is working, the new user may return the device to the place of purchase for a refund. The returned device having been opened and placed in contact with the user's skin would not be marketable to another user.

False negative conclusions are harmful in that the cost of treatment goes up as functional units are discarded and the user may view the provider of the microcurrent therapy devices in a negative light for providing non-functioning units.

One possible solution is the addition of a switch to the MCTD. Under this solution, the MCTD is activated by pressing downward on the center of the MCTD. The unit is equipped with a small pressure activated switch that provides both an audible sound and a small mechanical vibration to provide a tactile feel to the person activating the unit. Although the addition of a pressure activated switch would be an improvement over prior art solutions, the use of a switch is imperfect as someone who has operated the switch may not be sure if it worked, or may activate the switch several times to see if the MCTD current can be perceived. One problem with operating a switch several times is that the user may lose confidence that the user remembers how many times the switch has been activated. The user may wonder "Was it an odd number of times (the unit is on) or an even number of times (the unit is off)"? If the user is unable to perceive the flow of the microcurrent, the user is now tempted to keep switching the unit on and off throughout the period of intended application to hedge the user's bet. Unfortunately hedging the bet on switch position leads to undesired interruptions in the application of microcurrent therapy.

Another potential solution is the use of an indicator such as an LED corresponding circuit such as used in the D'Alerta device. However, the LED indicator wired as shown in the D'Alerta device would be only a partial solution since the LED would merely indicate that the battery is working and would not provide an indication on the existence of substantial current flow the tissue.

Thus, the prior designs do not provide a suitable solution to the problem of determining whether an imperceptible amount of current is passing through the user's skin and the underlying tissue.

A solution to the problem must not cause other undesired consequences in the context of applying therapeutic microcurrents for extended periods to ambulatory users. The therapeutic device needs to be suitable to affix to a variety of locations on a human body. The therapeutic device needs to move with the user for an extended period of time (on the order of days or weeks). The microcurrent therapy device needs to be designed so that it can be used during physical activity including but not limited to golf, swimming, tennis, basketball, biking, and long distance running. In order to reduce the problems associated with limiting or inhibiting movement, it is important for the device to be flexible and have a low profile so that the device is more like another set of skin than an electrical box taped to the user. Having a low profile increases the chance that the user can wear his or her regular sports clothing, including the various types of tight fitting clothing used for various sport activities.

Because a microcurrent device is typically used for an extended period of time, it is important to provide a device that will provide a relatively uniform current flow over the intended period of use.

It is an advantage to create a device that consumes power sparingly so that the useful life of the microcurrent therapy device is extended for a given battery. While it could work to add additional batteries or a battery with a longer life to the microcurrent therapy device, these additional or more powerful batteries add some combination of size, weight, or cost to the microcurrent therapy device.

In order to keep costs down, it is preferred that the microcurrent therapy device be able to use readily available batteries so that the non-recoverable engineering costs of establishing a process and an assembly line for a battery is amortized over so many batteries that it becomes essentially negligible.

SUMMARY OF THE INVENTION

Briefly, the present invention is directed to an electronic stack that can be placed in a microcurrent therapy device in electrical connection with the user's skin and in electrical connection with the other skin contact plate. The present invention includes a profile minimizing system of using an off the shelf "coin" battery within the electronic stack. The present invention includes an indicator (in this case an LED light) to indicate that the current path through the skin is operating. The circuitry chosen for this device provides a relatively uniform delivery of therapeutic microcurrent over an extended period of time by making efficient use of power drawn from the battery.

DETAILED DESCRIPTION OF THE DRAWINGS

Overview of the MCTD

Figure 1:
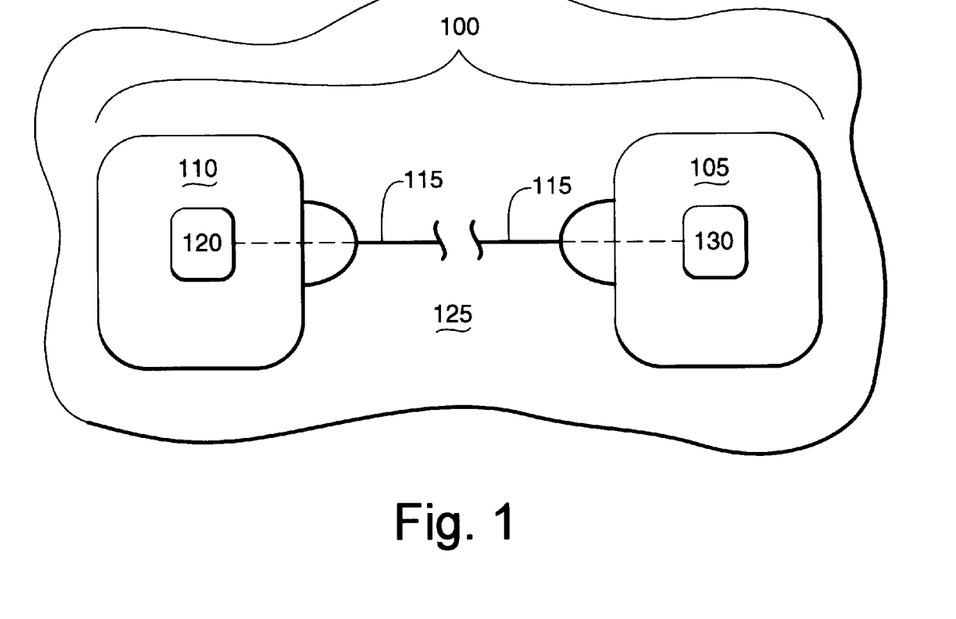
FIG. 1 is a top view of a preferred embodiment of the present invention for a Microcurrent Therapy Device (MCTD).

FIG. 1

Referring first to FIG. 1, the figure contains a top view of a preferred embodiment of the present invention. FIG. 1 introduces the elements of the MCTD to provide a general orientation before subsequent drawings introduce the elements within the pads. The MCTD 100 is comprised of a stack pad 105 and a plate pad 110 connected by an connection wire 115. The path of therapeutic current flow includes a path from the battery hidden within the stack pad 105 through the connection wire 115 to the plate pad 110 down through the plate pad 110 to a plate side electrode pad 120 in electric contact with the skin of the user 125 below the plate pad, through the user 125, back to a stack side electrode pad 130 below the stack pad 105 and back to the hidden battery. As discussed in subsequent figures, the stack pad 105 contains additional electrical components so the actual path of therapeutic current flow from one side of the battery to the other involves other electrical components. Additional path or paths for current flow run through various devices in the stack pad without leaving the stack pad. 105.

The discontinuity in the drawing of connection wire 115 indicates that the length of the connection wire can be varied to at the manufacturing stage to vary the maximum possible distance between the stack pad 105 and the plate pad 110.

The choice of whether the plate pad 110 serves as the cathode or the anode is arbitrary as long as the internal circuitry is designed such that the biasing voltages and polarities of components are kept in mind while implementing the circuits disclosed in this application. The preferred embodiment uses a Lithium "coin" battery of the general type shown in U.S. Pat. No. 5,931,693. As best shown in FIGS. 12 and 13 of the U.S. Pat. No. 5,931,693, a shell comprising the top, side, and the outer annulus of the bottom of the battery is positively charged and the inner area of the bottom of the battery is negatively charged. As discussed in greater detail below, the battery clip of the present invention connects the positive outer shell to the stack side electrode pad 130. Depending on what other changes were made to the circuit, reversing polarity while taking advantage of the inventive battery clip would require obtaining coin batteries with a negative shell and then adjusting the components within the circuit (to be described below) accordingly.

Figure 2:
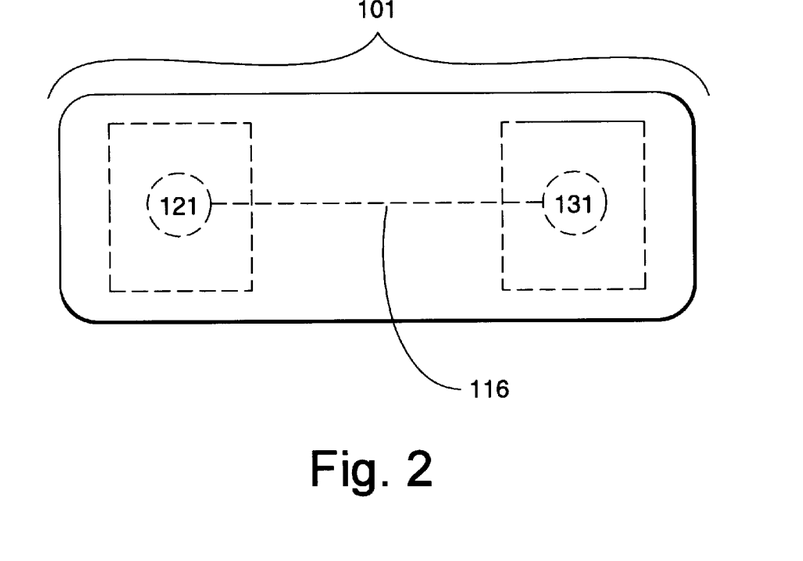
FIG. 2 is a top view of a alternative embodiment of the present invention for a MCTD.

FIG. 2

Turning now to FIG. 2, an alternative embodiment of the present invention is presented as viewed from the top. In this embodiment the alternative MCTD 111 has the two pads 121 and 131 placed at substantially opposite ends of an embodiment that resembles a common adhesive bandage. The two pads 121 and 131 are connected indirectly through connection wire 116 which runs internally through the MCTD 101. For this embodiment, the preferred configuration has the stack pad at one end and the plate pad at the other. A variation (not shown) would be to place most of the stack pad approximately halfway along the length of the MCTD 101 and have a first and a second plate pad at either end of the MCTD 101.

The Basic Circuit

Figure 3:
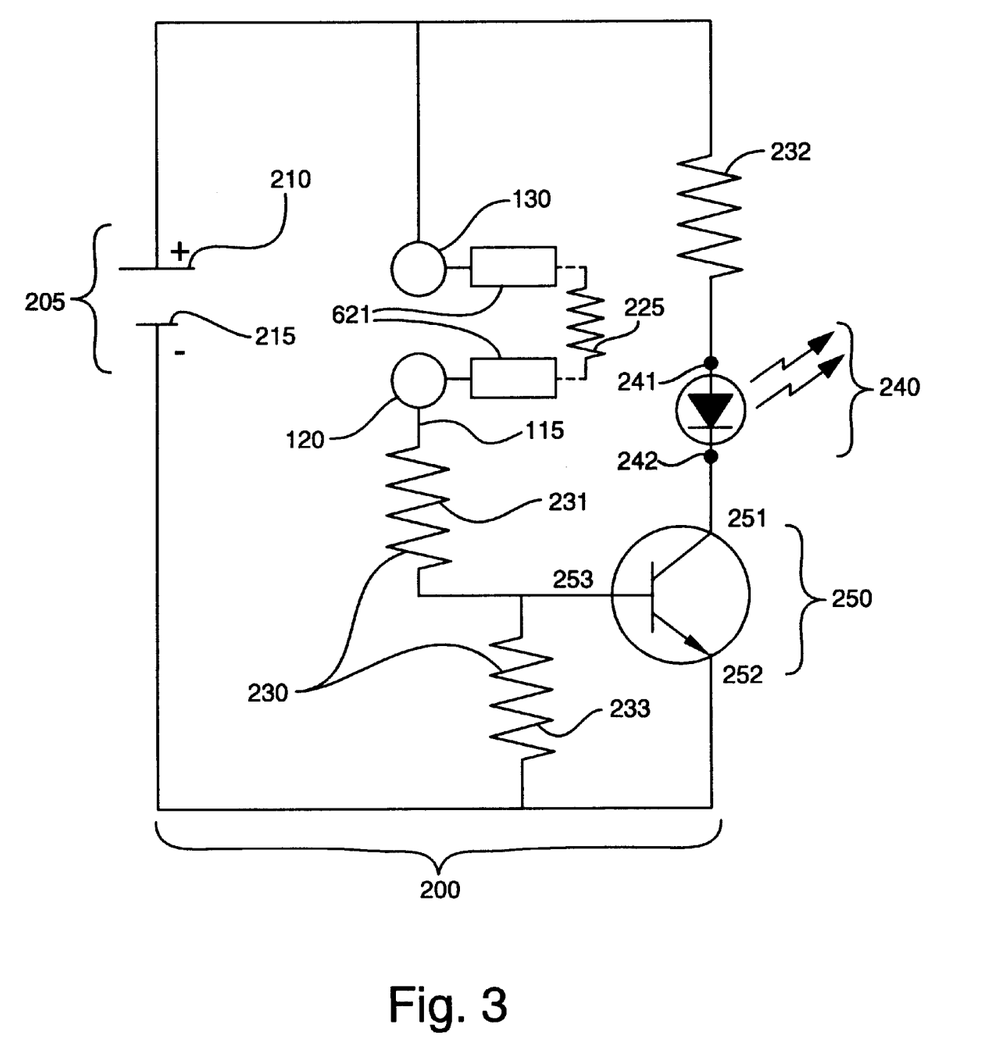
FIG. 3 is a schematic diagram of a basic circuit suitable for use in the present invention for a MCTD.

FIG. 3

Moving to FIG. 3, an embodiment of the circuit for the present invention is disclosed in schematic format. The circuit components are selected to balance one another and provide the functions described below. After seeing this or other circuits disclosed in the patent, a circuit designer of ordinary skill in such art could easily generate other substitute circuits that provide the same functionality. Depending on the type of components used for the various functions, the schematic of the substitute circuit could appear quite different from the disclosed circuit while still falling within the scope of the claims that follow this description.

The components of the circuit include connections to a power supply which in this case is a battery 205. The preferred mode of operation of the present invention is a MCTD that can move with the user without attachment to a non-moving fixture such as a wall outlet with a transformer. The mobility could be achieved by a small solar panel in electrical connection with the MCTD or other suitable power supplies for providing the voltage and current levels required for this application. A suitable battery for this application is a lithium coin battery such as a Renata model number CR1620.1B (P189-ND). The circuitry described below will operate for an extended period of continuous operation on a 3 volt battery with a rated life of 75 milliampere hours (mAHrs.). The useful life for continuous operation can exceed several weeks. Advantageously, a plastic storage pad is provided with the MCTD so that the MCTD can be removed by the users and placed into a storage mode that does not continue to drain the battery. Use non-use intervals for a MCTD are beyond the scope of this disclosure but may include choice to remove the device before showering, to use the MCTD only during exercise, to use the MCTD only after exercise, or to apply the MCTD for periods of several days at a time. Thus, it is advantageous to have a place to store the MCTD when not in use. To reduce the rate of absorption of moisture from ambient air, the plastic storage pad with the attached MCTD can be placed within a re-sealable moisture impermeable bag such as those with a zip lock fastener.

First Path for Current

The first path for current between the positive terminal connection 210 and the negative terminal connection 215 runs from the positive terminal connection 210 to the stack side electrode pad 130 through the microcurrent electrode 621 (described below in connection with FIG. 7) to the skin of the user 125 as represented by user tissue resistance 225 to the microcurrent electrode 621 in contact with the plate side electrode pad 120. In the preferred embodiment the plate side electrode pad 120 is connected by connection wire 115 to the electrical components in the stack pad.

The flow path continues through a voltage divider 230 back to negative terminal connection 215 to complete the first flow path. In the preferred embodiment the voltage divider 230 has resistance device 231 and resistance device 233. The full purpose of voltage divider 230 will become apparent in the discussion below. The present embodiment of this circuit uses a 56 KΩ resistor for resistance device 231 such as a Panasonic 0603, P56KGCT-ND. (Nominal size 0.006 inch by 0.003 inch). The present embodiment of this circuit uses 1 Meg Ω resistor for resistance device 233 such as a Panasonic 0603, P1.0MGCT-ND.

The Second Path for Current

The second path for current starts at the positive terminal connection 210 and passes through resistance device 232 to indicator 240 at the first side 241 of indicator 240. A 2.7 kΩresistor is used for resistance device 232 in the current embodiment of this circuit. The second path for current continues from the second side 242 of indicator 240 to the first side of switch 250. When the switch is closed the current path continues from the second side of the switch 250 back to the negative terminal connection. The switch is conductive between the first side 251 and the second side 252 during the application of a control signal to switch input 253.

The switch input 253 is electrically connected to the voltage divider 230. In this embodiment of the circuit the connection is between resistance devices 231 and 233.

The current preferred implementation is to use an LED for the indicator 240. A suitable LED is a Liteon 160-1166-1-ND but other LEDs with a turn on voltage of 1.8 volts may be used.

The current preferred implementation for this circuit uses an NPN transistor as switch 250 with first side 251 connected to the collector, and second side 252 connected to the emitter, and switch input 253 connected to the base such that when a control signal is applied to switch input 253 the path between sides 251 and 252 becomes conductive completing the second current path and thus activating the indicator 240. The activated indicator 240 which is a LED in the preferred embodiment provides a constant emission of light to indicate that the MCTD has both an operating power supply and a current flow through the user (as represented here by user tissue resistance 225). If current flow through the user (225) ceases, the first path for current flow will stop and the voltage divider 230 will stop providing the requisite control signal to switch input 253. The lack of the requisite control signal to switch input 253 will end the conductive path between sides 251 and 252 thus stopping the operation of indicator 240. A suitable NPN transistor would be an FMMT2222ACT-ND manufactured by ZETEX. Other switching devices could be substituted for the NPN transistor providing that the flow path through the indicator is interrupted when the current flow between 120 and 130 is below the target level for current flow.

Alternative Indicators

Indicator 240 does not have to be a continuously operating LED. Indicator 240 could be any other suitable indication including audible or vibratory indications in addition to visual indications. Indicator 240 is a continuous indicator in this embodiment but could be substituted with an indicator having its own timing circuit to provide a non-continuous indication such as a blinking LED. The use of a blinking light rather than a continuously burning light will decrease the drain on the battery.

Indicator 240 could have its own switch which would selectively break open the second path for current flow so that the indicator 240 could be selectively turned on and off. Thus indicator 240 would need both switch 250 and its own switch to be closed so that current can flow through the second path for current and provide power to indicator 240.

A Circuit with an Intermittent Indicator Signal

Figure 4:
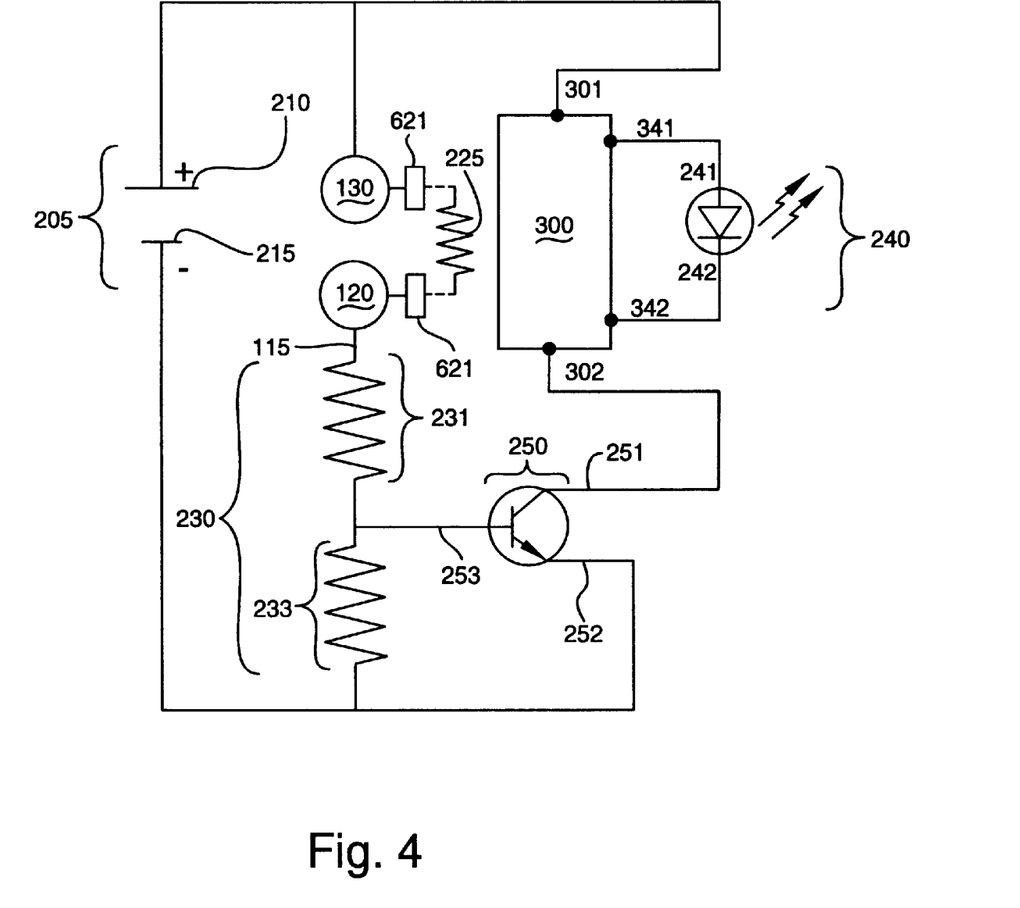
FIG. 4 is a schematic diagram of a circuit for use in the present invention for a MCTD adapted to incorporate an indicator timing circuit in addition to the components indicated in FIG. 3.

FIG. 4.

Turning now to FIG. 4, a schematic diagram shows a variation of the circuit disclosed in FIG. 3. In this variation elements 205, 210, 215, 130, 621, 225, 120,115, 230, 231, 233, 240, 241, 242, 250, 251, 252, 253, perform the functions described above and thus will receive only passing mention here. The suggested components for the Basic circuit are suitable for like numbered elements in FIG. 4.

The difference between FIG. 3 and FIG. 4 is the inclusion of indicator timing circuit 300 ("ITC"). ITC 300 is effectively inserted for indicator 240 and resistance device 232 in the second flow path for current by connections at junctions 301 and 302. At times determined by the operation of the indicator timing circuit 300, the voltage potential between indicator control junction 341 and indicator control junction 342. When the proper voltage differential exists for indicator 240, a current path is established between junction 301, junction 341, first side 241, through indicator 240, out second side 242, to indicator control junction 342, and out junction 302 to first side 251 of switch 250.

Thus as before, indicator 240 cannot be activated without current flow through tissue resistance 225. However the addition of the ITC 300 provides a second level of control over indicator 240 so that both switch 250 and ITC 300 must be operating to enable current flow through indicator 240.

Figure 5:
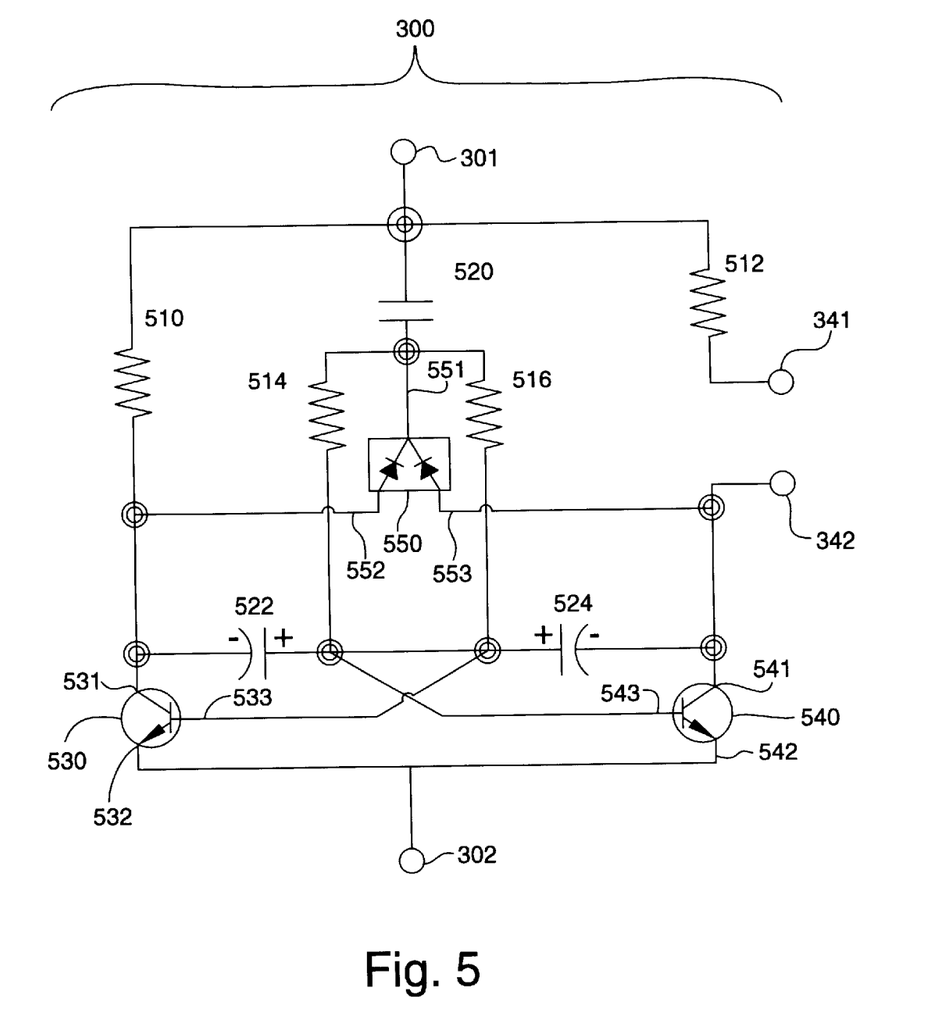
FIG. 5 is a schematic diagram of an exemplary indicator timing circuit for use in an embodiment of the present invention having a blinking indicator light or other alternating indicator.

The required characteristics for the voltage potential and current flow between junctions 341 and 342 are determined by the type of indicator used for indicator 240 and the value of resistor 512 (visible in FIG. 5). The choice of resistors here allows the designer to choose the level of current flow through the indicator light. Thus the circuit can be constructed so as to increase the brightness of the indicator lamp at the expense of decreased battery life, or decreased brightness so as to extend battery life for a given battery.

Many possible circuits could provide some form of alternating output across junction 341 to junction 342. The indicator could be generally on with a brief periodic interruption, or generally off with a brief periodic operation of the indicator.

The advantage of having an indicator that alternates between on and off varies with the type of indicator. If the indicator is a LED as is used in the preferred embodiment, the alternation between on and off can provide a visual clue that the unit is operating even when the indicator LED is viewed in an environment with bright ambient light such as a sunny tennis court or the beach. If the indicator uses an audible tone, then a periodic chirp would be preferred over a constant drone.

Exemplary Indicator Timing Circuit

FIG. 5.

The current preferred embodiment for ITC 300 is shown as a circuit diagram in FIG. 5. The four junctions discussed in FIG. 4 (301, 302, 341, and 342) are indicated on FIG. 5. Junction 301 is connected to three components, resistive device 510, resistive device 512, and capacitor 520. The dual polarized capacitors 522 and 524 are alternately charged and discharged by the operation of ITC 300. As these capacitors 522 and 524 are alternately charged and discharged, the NPN transistors 530 and 540 receive and lose the requisite control voltage at their respective base nodes 533 and 543. The flow of current from junction 342 can only reach junction 302 through transistor 540. Although junction 342 is electrically connected to the anode 553 of dual diode 550, non-transient current cannot flow from anode 553 to cathode 551 because cathode 551 will be at a higher voltage than anode 553. Nor can non-transient current flow from junction 342 across capacitor 524 as capacitor 524 is polarized in the wrong direction for such current flow.

The opening and closing of the path for current flow between collector 541 and emitter 542 causes a corresponding opening and closing of the path for current flow from junction 341 to junction 342. Element 550 and non-polarized capacitor 520 are used to start the oscillation between both transistors so as to ensure that the circuit oscillates to produce the desired blinking. RC timing circuits using resistive device 514 and resistive device 516 together with capacitor 522 and capacitor 524 create the time constants for the on and off phase of each transistor (530 and 540).

The Arrangement of the Stack in the Stack Pad

During the discussion of FIG. 1, the discussion did not include any details of the various layers and components that go into the stack pad 105. The details of the stack pad represent one inventive aspect of the present invention and will be set forth in the text that follows.

Figure 6:
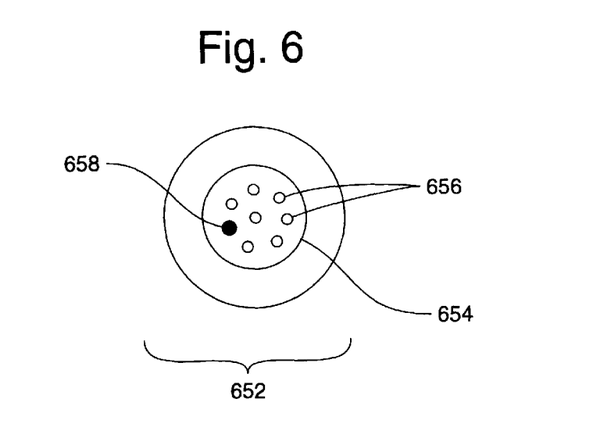
FIG. 6 is a view looking up at the bottom of circuit board used in the present invention for a MCTD illustrating the use of a battery pad that is sized to fit within the negative terminal of the coin battery.

FIG. 6

Turning now to FIG. 6, the bottom of circuit board 652 is illustrated. An inventive aspect of this circuit board is that the circuit board contains a battery pad 654 that is sized to fit within the negative terminal of the coin battery 205 without touching the annular portion of the positive terminal of the coin battery 205. In the preferred embodiment, the battery pad 654 is tin-plated and has a number of protrusions 656 to promote and ensure a reliable electrical contact with the negative terminal of the coin battery 205.

The electrical connection with the negative terminal of the coin battery 205 is extended from the battery pad 654 to the negative terminal connection 215 shown in FIG. 4 by a through connect 658. The through connect 658 can be constructed from any standard process such as those used for creating a plated through hole connection (PTH).

Figure 7:
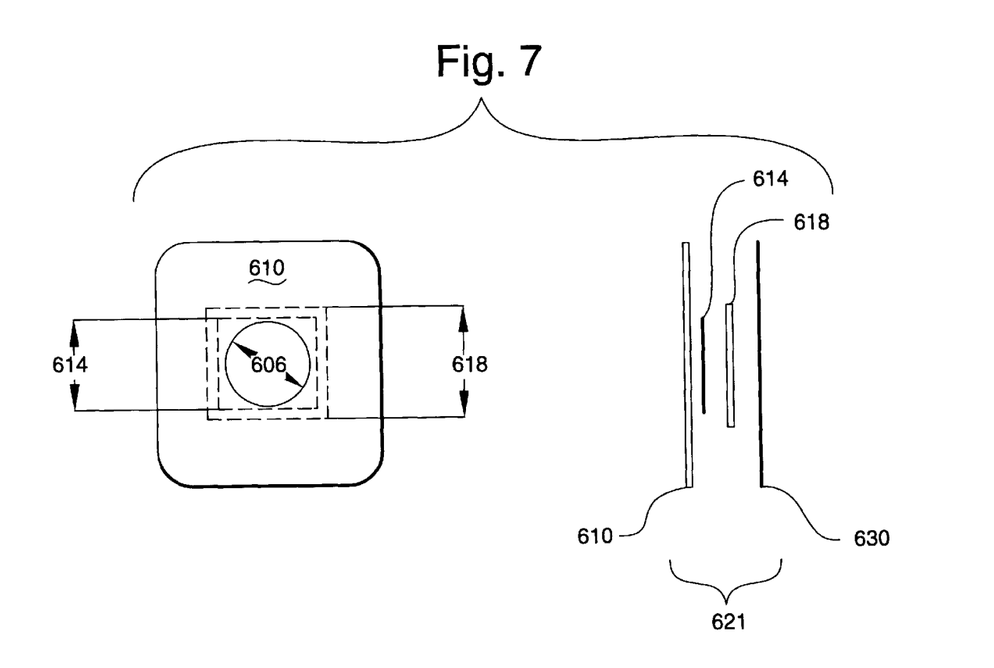
FIG. 7, shows a component of the MCTD, the microcurrent electrode 621 as shown from two views, from above and from the side with the components separated to show detail.
Figure 8:
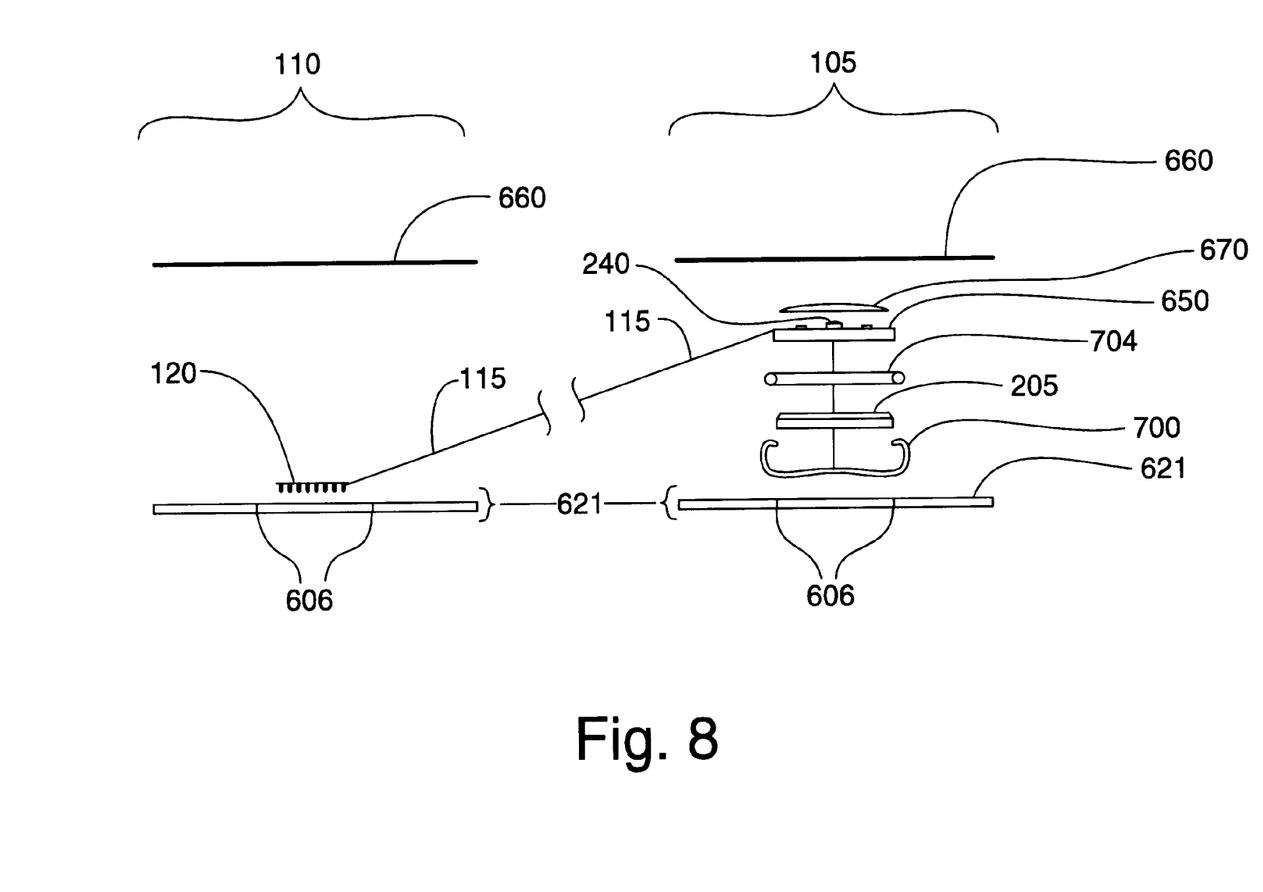
FIG. 8 is an exploded side view of the various components of the present invention for a MCTD in the embodiment shown in FIG. 1.

FIGS. 7 & 8

Moving first to FIG. 8, the various layers of the stack pad are set forth. As discussed above, the preferred embodiment uses a lithium coin battery 205. The positive terminal for the battery covers the top, side, and outer annulus of the lower face of the coin shaped battery. However, the present invention uses the coin shaped battery in an inverted position so that the positive side of the battery is placed facing down toward the user's skin.

The positive terminal of the coin battery is in contact with battery clip 700 (which will be described in more detail below). Battery clip 700 provides an electronic conduction path between the positive terminal of the battery and the microcurrent electrode 621. The details for microcurrent electrode are best seen in FIG. 7. In FIG. 7, the microcurrent electrode 621 is shown from two views, from above and from the side with the components separated to show detail. The bottom of battery clip 700 fits within an opening 606 in bottom carrier 610 so that the bottom carrier does not interfere with the electrical contact between the bottom of the battery clip and the rest of the microcurrent electrode 621. A preferred material for bottom carrier 610 is Avery Med. number 5322 or equivalent tan colored spunlaced nonwoven polyester fabric.

The bottom of the battery clip 700 makes electrical contact with conductive pad 614. Preferably the conductive pad 614 is a carbon film with silver coating on the gel side with a flat profile approximately 0.004 inches thick. Carbon film is preferred over metallic or other rigid materials for two reasons. First, metal electrodes can lead to localized arcing under certain conditions. Second, rigid components can be somewhat irritating when placed on the skin above spinal column since the rigid electrode would tend to rub the bones in the spinal column during use.

The conductive pad 614 is covered by a larger zone of conductive gel 618. A preferred material is a solid hydrogel of the type used in TENS units. The use of a solid hydrogel eliminates some of the variability in electrical conductivity since the end user does not need to decide whether to apply a conductive gel to the electrode and the gel is applied in a uniform manner. Further the solid hydrogel is not apt to partially rub off before the device is applied to the target section skin. A layer of adhesive 630 covers the conductive gel 618 and the exposed bottom of the bottom carrier 610 without blocking the electrical conductivity between the conductive gel 618 and the tissue of the one who will use this MCTD. Thus ending the electrical conduit path between the battery clip and the tissue of the person receiving therapy.

Continuing with the discussion of the elements shown in FIG. 8, an encapsulation layer 670 covers the various components of the circuit assembly 650. The encapsulation layer improves the durability of circuit assembly 650. The preferred material for the encapsulation layer 670 is a clear epoxy.

The indicator 240 in the preferred embodiment is a LED which is placed so that the LED shines through top cover 660. In the preferred mode, the LED shines through a small hole in the top cover, but a transparent window could be used over the LED as an alternative.

The assembly of the plate pad 110 to create an electrical conduit path to the tissue of the person receiving therapy follows the same principles set forth for the stack pad 105 with the substitution of the plate side electrode pad 120 in place of the various components found in the stack pad 105.

Figure 9:
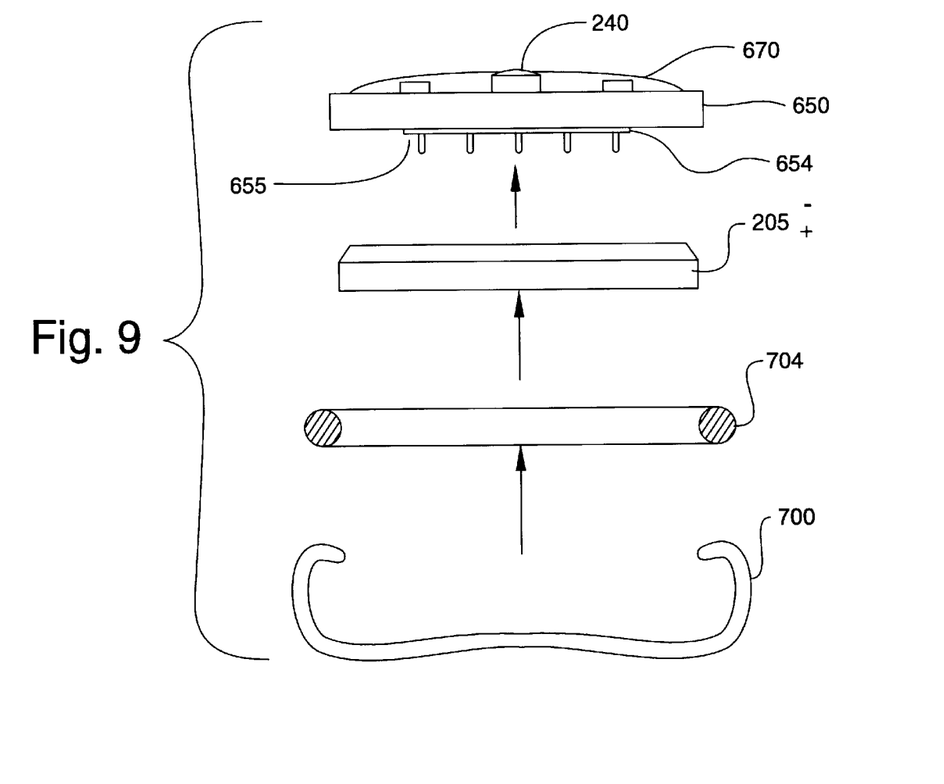
FIG. 9 shows the assembly steps for a sub-set of components within the MCTD, specifically the sub-set of components to be held by the battery clip.
Figure 10:
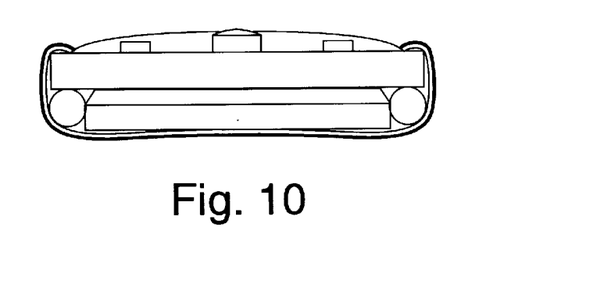
FIG. 10 shows the same components shown in FIG. 9 after the completion of the sub-assembly.

FIGS. 9 & 10

In order to focus on one portion of the path for current flow from one end of the coin battery 205 to the other, please turn to FIGS. 9 and 10. FIG. 9 shows the assembly steps for a portion of the device. FIG. 10 shows these components after assembly. In FIG. 9, the circuit assembly 650 is shown without its protective layer of encapsulate 670. The battery pad 654 on the bottom of circuit board 652 is just a thin line from this view, but provides a path for connecting the circuit to the negative side of inverted coin battery 205. A layer of conductive epoxy 655 is applied to the bottom of the battery pad 654. The coin battery 205 is applied to the conductive epoxy 655 and allowed to cure for 24 hours or as appropriate for epoxy used.

After the epoxy curing, an O-ring 704 is stretched over the coin battery 205. For the battery identified above, the preferred Oring is a standard 18 mm (O.D.), 15 mm (I.D.), and 1.5 mm thick O-ring made from BUNA N.

After the Oring 704 has been applied, a battery clip 700 is applied. The battery clip 700 provides a conductive path to connect the circuit to the positive side of the coin battery 205.

FIG. 10 illustrates the relative position of the various components when assembled. Note that after assembly, the encapsulate layer 670 is added to encapsulate the circuit components and the tips of the battery clip 700. Indicator 240 is visible protruding through the top of the encapsulate 670.

The preferred material for the battery clip 700 is stock that is 0.006 inch thick ETP copper which has received a nickel electroless plating. Other suitable materials could be substituted for ETP Copper however ETP Copper is the preferred material because of its favorable blend of useful characteristics. Electrolytic Tough Pitch copper (ETP copper or ETPC) has the highest degree of electrical conductivity of any metal except silver. ETP copper has relatively high ductility which gives it favorable qualities in various machining and forming operations. ETP copper can be cold-worked or hot-formed and is readily used in manufacturing steps that call for either welding or soldering. In addition the corrosion resistance of ETP copper is excellent when compared with other comparable materials.

Those skilled in the art will recognize that the methods and apparatus of the present invention has many applications and that the present invention is not limited to the specific examples given to promote understanding of the present invention. Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A stack of components for use in a microcurrent therapy device (MCTD) comprising:
   a coin battery with a first terminal and a second terminal;
   a circuit board with components for an electric circuit used in the MCTD;
   a battery pad adjacent to the bottom of the circuit board and electrically connected to a portion of the electric circuit;
   the battery pad sized to contact the first terminal without touching the second terminal of the coin battery that encircles the first terminal;
   a battery clip adapted:
   1) to provide an electrical connection from the second terminal of the coin battery to the top face of the circuit board; and
   2) to maintain a compressive force on a subassembly of the MCTD comprising the circuit board, battery pad, coin battery, and battery clip.

2. The MCTD of claim 1 further comprising
   an O-ring of appropriate size to be stretched to fit over the radial perimeter of the coin battery before the application of the battery clip.

3. The MCTD of claim 1 further comprising a layer of conductive epoxy used to adhere the battery pad to the circuit board.

4. The MCTD of claim 1 further comprising a through connect located within the circuit board to provide an electrically conductive path from the bottom side of the circuit board to the electrical circuit on the circuit board.

5. The MCTD of claim 1 further comprising
   an encapsulation layer over a set of circuit elements on the top side of the circuit board.

6. The MCTD of claim 5 wherein the encapsulation layer does not fully cover an indicator element on the top side of the circuit board.

7. The MCTD of claim 1 further comprising:
   1) a first connection wire connected at one end to the stack and at the other end to a first electrical conduit path adapted to be connected to tissue; and
   2) a second connection wire connected at one end to the stack and at the other end to a second electrical conduit path adapted to be connected to tissue
   whereby the MCTD is adapted to allow a flow of current from one terminal on the coin battery to the other terminal on the coin battery through a route that includes:
   A) traveling from the stack along the first connection wire;
   B) through the first electric conduit path adapted to be connected to tissue;
   C) through the tissue of the person receiving therapy;
   D) through the second electrical conduit path adapted to be connected to tissue; and
   E) through the second connection wire to the stack.

8. The MCTD of claim 1 further comprising:
   1) a first connection wire connected at one end to the stack and at the other end to a first electrical conduit path adapted to be connected to tissue; and
   2) a second electrical conduit path adapted to be connected to tissue is placed essentially below the stack and in electrical connection with the battery clip
   whereby the a flow of current from one terminal on the coin battery to the other terminal on the coin battery includes traveling through tissue located essentially below the stack and tissue below the first electrical conduit path to tissue.

9. A MCTD pad for use in a MCTD comprising
   1) a top layer;
   2) a bottom layer;
   3) a layer of one or more electrical components positioned in-between the top layer and bottom layer;
   4) a carbon film conductive pad in positioned below the bottom layer but in electrical contact with the layer of one or more electrical components by an opening in the bottom layer;
   5) a layer of conductive gel applied to the bottom layer of the conductive pad;
   6) a layer of adhesive on the bottom of the bottom layer; and
   7) a battery clip that provides:
   1) a first electrical connection between a first terminal of a coin battery and the conductive pad; and
   2) a second electrical connection between the first terminal of the coin battery and a battery terminal input on a circuit board containing the electrical components used in the MCTD.

* * * * *